(12) United States Patent
Friberg et al.

(10) Patent No.: US 6,782,888 B1
(45) Date of Patent: Aug. 31, 2004

(54) BREATHING APPARATUS

(75) Inventors: Harri Friberg, Buchs (CH); Jakob Däscher, Buchs (CH)

(73) Assignee: eVent Medical Ltd., Carlsbad, CA (US)

( * ) Notice: Subject to any disclaimer, the term of this patent is extended or adjusted under 35 U.S.C. 154(b) by 0 days.

(21) Appl. No.: 09/958,520

(22) PCT Filed: Apr. 3, 2000

(86) PCT No.: PCT/IB00/00407
§ 371 (c)(1),
(2), (4) Date: Feb. 12, 2002

(87) PCT Pub. No.: WO00/59566
PCT Pub. Date: Oct. 12, 2000

(30) Foreign Application Priority Data
Apr. 7, 1999 (CH) .................................................. 652/99

(51) Int. Cl.[7] .................................................. A62B 7/00
(52) U.S. Cl. ............................ 128/204.18; 128/203.12; 128/203.13; 128/205.24

(58) Field of Search .................. 128/203.12, 205.24, 128/204.18, 204.21, 204.23, 203.13, 205.11

(56) References Cited

U.S. PATENT DOCUMENTS

| | | | | | |
|---|---|---|---|---|---|
| 4,794,922 A | * | 1/1989 | DeVries | ................ | 128/204.18 |
| 4,870,961 A | * | 10/1989 | Barnard | ................ | 128/202.27 |
| 4,905,688 A | * | 3/1990 | Vicenzi et al. | ......... | 128/204.21 |
| 5,549,105 A | * | 8/1996 | Bloch et al. | ........... | 128/203.12 |
| 5,676,133 A | * | 10/1997 | Hickle et al. | .......... | 128/205.12 |
| 5,694,926 A | * | 12/1997 | DeVries et al. | ........ | 128/205.24 |
| 6,536,430 B1 | * | 3/2003 | Smith | .................... | 128/204.18 |
| 6,543,449 B1 | * | 4/2003 | Woodring et al. | ..... | 128/204.18 |
| 6,571,792 B1 | * | 6/2003 | Hendrickson et al. | . | 128/203.12 |

* cited by examiner

Primary Examiner—Amanda R. Flynn

(57) ABSTRACT

The invention refers to a new type of ventilator, which has a compact block, in which rigid pipes and a gas supply container are integrated. The new structure is more compact than conventional superstructures. In addition to this improvements have been made to the therapy gas delivery and nebulization.

30 Claims, 3 Drawing Sheets

BREATHING APPARATUS

CROSS-REFERENCES TO RELATED APPLICATIONS

Not applicable.

STATEMENT REGARDING FEDERALLY SPONSORED RESEARCH OR DEVELOPMENT

Not applicable.

BACKGROUND OF THE INVENTION

The invention refers to a ventilator.

TECHNICAL FIELD

Ventilators are used to either ventilate patients who have breathing difficulties or a loss of lung function, or they are used as gas mixing devices to condition the air inhaled by a patient. They therefore have ventilator gas connections, valves, controls for the valves and pressurised gas connections, to create gas pressure to inject air into the ventilating tubes or patient's lungs.

In operation the pressurised gas connections are often connected to a compressed air system, where the compressed air in the device operates a pneumatic pump, which transports the ventilator gases. However, the ventilator gases can be injected under pressure through the actual ventilator gas connections, meaning that the pressure required for ventilation is provided by the ventilator gases themselves. Ventilators do exist which can be attached to a compressor, which creates the necessary ventilator gas pressure when in operation and injects this into the ventilator.

Conventional ventilators therefore consist of a housing unit, which contains the gas supply container, valves, controls and possibly batteries as emergency power supply for the electrical valve controls as well. The housing also contains the ventilator gas connections and connections for the ventilating tubes mentioned above. The connections are connected to the valves and the gas supply container via tubes inside the device. As these tubes take up a certain amount of constructional volume and adequate space must be available to fit these tubes, conventional ventilators must be of a certain size.

SUMMARY OF THE INVENTION

The invention aims to reduce the constructional size of a ventilator. This task is solved by the distinctive features. The first step of the invention is to replace the tubes with rigid pipes. The second step of the invention is to integrate the tubes with the gas supply container, thus forming a compact block of plastic or metal. The invention then foresees the consequent integration or flange-mounting of the necessary valves and gas connections in/on this block. This produces a very compact design for the device.

Further developments for the invention, which could in principle also be used independently of the inventive concepts above, include the following particular points:

The integration of a compressor in the housing, where the compressor's pressure output could be connected to the block via a tube to allow vibration-free coupling of pressure between the compressor and the block.

Heated gas feeds, by using the heat generated by the compressor's activity to prevent the undesirable formation of condensation in the ventilator gas.

To achieve complete electrical self-sufficiency, where all electrically operated parts, which also includes the compressor, can be supplied with power from an internal battery. This battery should ideally be the main source of energy and should only be given a constant mains boost or charge via a charger where a mains feed is available. With this invention, disconnecting from the mains supply will not therefore interrupt ventilation in any way. This also dispenses with the need to connect a compressed gas supply by means of a gas bottle, which was an essential accompaniment previously. This makes it easier to transport a patient who is on a ventilator, as the ventilator can be simply disconnected from the mains and moved with the patient.

An integrated charger for the integrated battery with a preferred design, with which any AC mains voltages between 80 and 270 V can be fed without the operating staff having to make any settings on the power unit.

An integrated connector to connect the ventilator's electrics or electronics with an external DC source, e.g. the on-board power supply of a motor vehicle.

A display, which is integrated in the housing, and a control panel. The preferred design for the latter is a push-and-turn knob, which permits single-handed selection of fields and buttons on the display. The electronics for this are programmed such that the selected fields appear highlighted in colour, thus making it easier and safer to use. The preferred design has additional keys, which are used to trigger instant control operations and program steps or settings.

Electrical interfaces in the housing, constituting a computer port (RS 232 interface), a nurse call, etc.

Sensors, either connected to or integrated in the block, which permit a patient's breathing activities to be monitored and these values to be reproduced on the display. A software, parameterised by the sensors, also allows control of ventilation depending on the measured parameters.

Proximal flow sensors, which can be connected to detect the patient's own attempts to breathe in the immediate proximity of the patient and deliver this to the electronics of the device.

A special, new and independently applicable software, which allows forced sigh ventilation to be set for any interval and any pressure and/or volume values. Sigh ventilation of this sort is a known feature, however state-of-the-art devices only allow this sort of ventilation to be carried out in an unspecific way. Hence sigh ventilation can be activated or deactivated in conventional devices—for example, every hundredth breath is performed with 120% of the normal breath volume and the lungs of the patient are therefore overstretched a bit with every hundredth breath. It was previously believed that this was sufficient, as a comparable sigh breath frequency had been established for the average patient. The inventor has however discovered that the average sigh ventilation is not always ideal. This sort of ventilation may even be painful for a patient following a recent ribcage operation, for example. The way that this invention can be set means that personal consideration can be given to each patient's requirements.

DESCRIPTION OF THE DRAWINGS

The figures describe a preferred design for the invention. This is an example and is not restrictive.

DETAILED DESCRIPTION OF THE INVENTION

The figures are described in general and the attached list of components forms part of the description. Additional benefits and features of the invention, as well as additional preferred formations, arise from the description of the figures.

Figure 4:
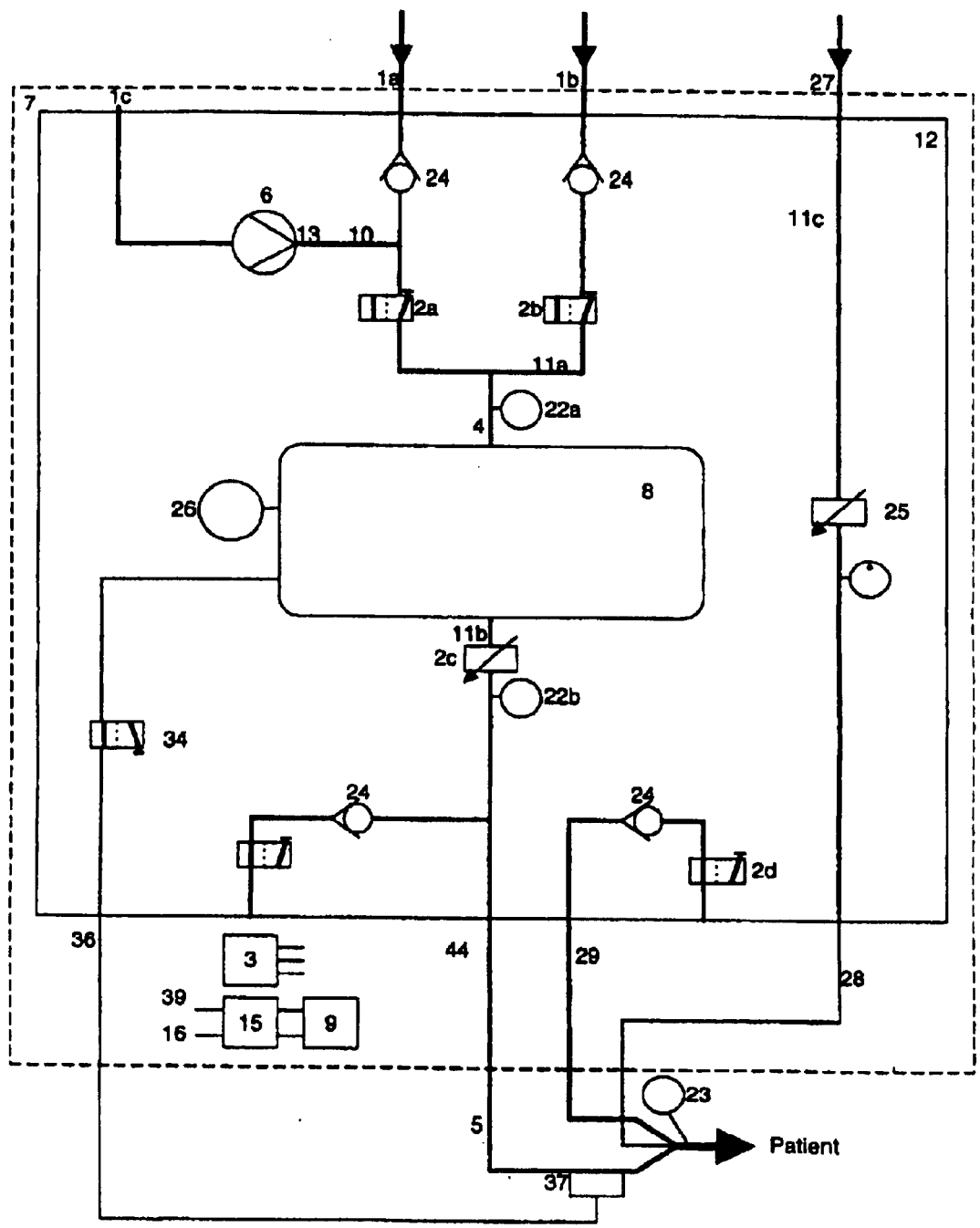
FIG. 4 A block diagram of the sample design.

The functionality and design of the preferred sample design can be seen in the block diagram in FIG. 4: on the input side you will see the gas connections—1c compressor input, 1a compressed air input, 1b ventilation gas input, e.g. oxygen input and 27 therapy gas input, e.g. for NO. The inputs are sighted on a block 12, which is found within the housing 7. Comprising compressor input 1c leads to a compressor 6, which is connected via a flexible pipe 10 with a rigid pipe 11a, which forms a compressed air pipe 4 to a gas supply container 8. Pipe 11a is interrupted by a valve 2a, which either feeds or blocks the compressed air from the compressor or from the compressed air connection 1a to the gas supply container 8. A similar ventilation gas valve 2b feeds or blocks the ventilation gas passage to pipe 11a from ventilation gas connection 1b (in this case oxygen, for example).

Parallel to the pipe 11a a rigid pipe 11c, is fed through block 12 or is designed in the block wall in particular. Pipe 11c connects the therapy gas connection 27 to the therapy gas output 28. Pipe 11c is divided by a controllable therapy gas valve 25. This design was preferable to the known superstructures, where the therapy gas pipes and therapy gas control valves were housed separately to the ventilator and therefore needed additional expenditure on equipment. The advantages over the known design include not only a reduced amount of housing and reduced structural volume, but it is also simpler to operate and clearer in use.

The gas supply container 8 is equipped with an oxygen sensor 26. On the output side it is connected to the ventilator tube 5 via a rigid pipe 11b. The rigid pipe 11b has a controllable inspiration valve 2c. The pressure and/or flow is measured before as well as after the gas supply container 8 via integrated sensors 22a and 22b. A proximal flow sensor 23 permits measurement of the patient's own breathing performance.

To administer medication and humidity a nebulizer pipe 36 is provided, which has a nebulizer valve 34 and nebulizer chamber 37. Various check valves 24 prevent loss of pressure if the connection tubes are disconnected. An expiration valve 2d terminates the expiration pipe 29. A ventilation tube 5, as well as a therapy gas output 28 if needed, run to the patient parallel to the expiration pipe 29.

The housing 7 also contains a control system or electronics 3, which are symbolically depicted and are especially connected to the electronically controlled valves and sensors. It also contains a battery or accumulator 9, which is powered from the charging equipment 15. A novel and preferential design of the charging equipment 15 allows it to connect to the DC power supply via a DC connection 16 on the one side and be charged with AC voltage of between 80 and 270 V via an AC connection 39 on the other side, without having to be set manually. Appropriate electronics are integrated in the charging equipment 15. The connection between battery 9 and charging equipment 15 is designed so that the battery receives a permanent charge all the time the charging equipment 15 is connected to the mains. If the external power supply fails, the system automatically switches to the internal battery.

In this sample design the block is divided into two—a lower section 12b and an upper section 12a. This is for assembly reasons and not essential. In the same way single piece or multi-piece blocks could be used for the invention.

Figure 3:
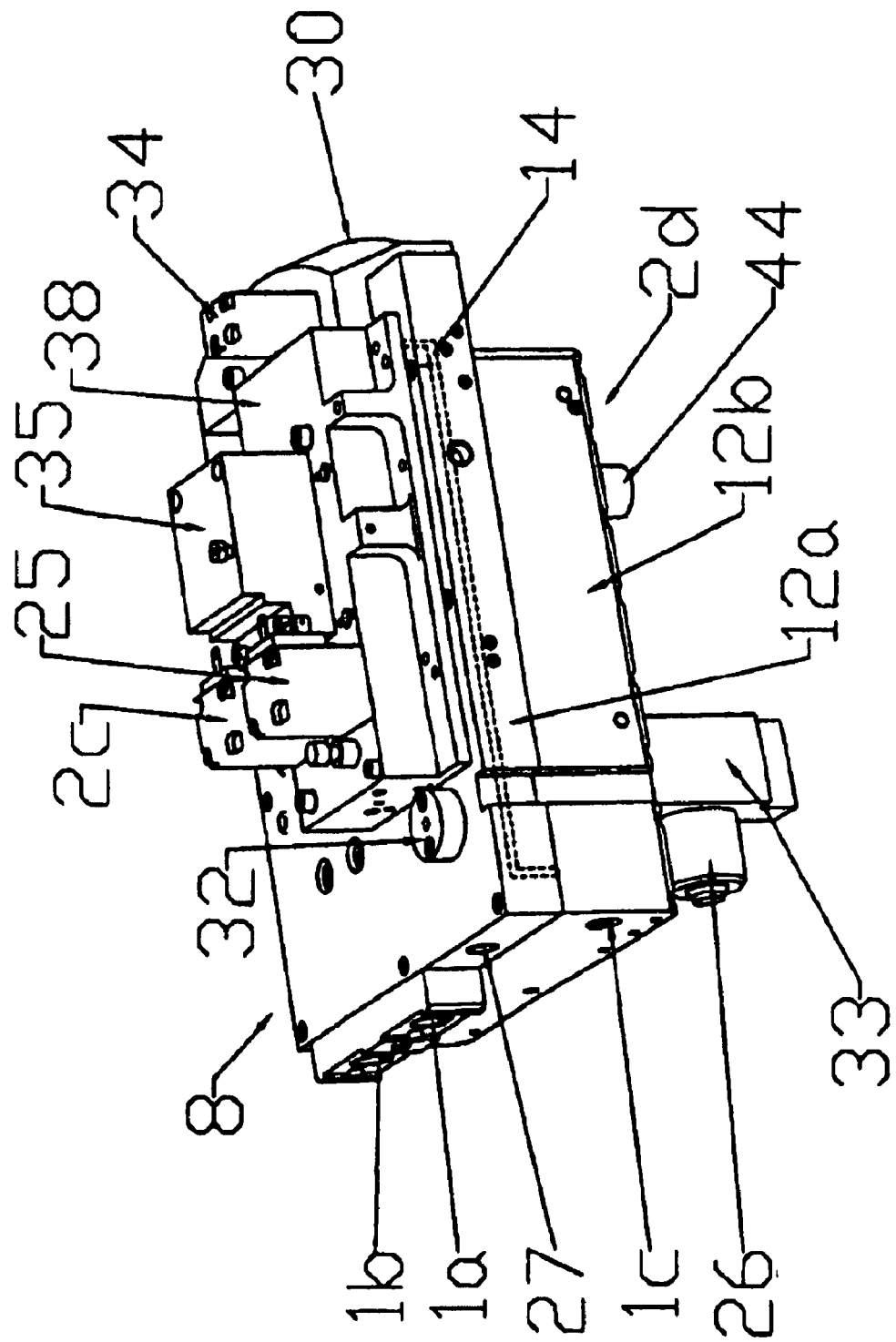
FIG. 3 The block feature of the invention as central part of FIG. 2.

As can be seen in FIG. 3 the lower section 12b includes an oxygen block 33 with oxygen sensor 26 and expiration valve 2d. In service the lower section 12b is screwed tightly to the upper section 12a to form the gas supply container 8 on the inside.

In this invention the shell walls of the upper and lower sections 12a and 12b contain rigid pipes which represent the gas routes according to the block diagram in FIG. 4. The gas supply pipes are at least 100 mm in length. A special pipe is represented by a broken line: gas deliverer 14 is a pipe which is connected to the compressor output 13. Compressed air leaving the compressor is warm when it is expelled. As this warm air has to travel a relatively long way through gas deliverer 14, this heat is released to block 12. This reduces the risk of condensation building up in the gas supply container 8. An alternative to the gas deliverer 14 shown here would be to use a longer, perhaps spirally rolled pipe inside the gas supply container 8 to access the compressor output 13.

Included in the upper section 12a are the compressed air and ventilator gas connections 1a and 1b, as well as therapy gas connection 27. It also carries a tank pressure control valve 32, the inspiration valve 2c, the therapy gas valve 25, and a safety block 35, which has a patient pressure relief valve and a patient suction relief valve. The last valves mentioned are equally located on valve block 38, which is designed as an integrated block and which incorporates the emergency valves and the devices for flow and pressure measurement in particular. The upper section 12a additionally carries a nebulizer valve 34 and the front connections 30.

Figure 2:
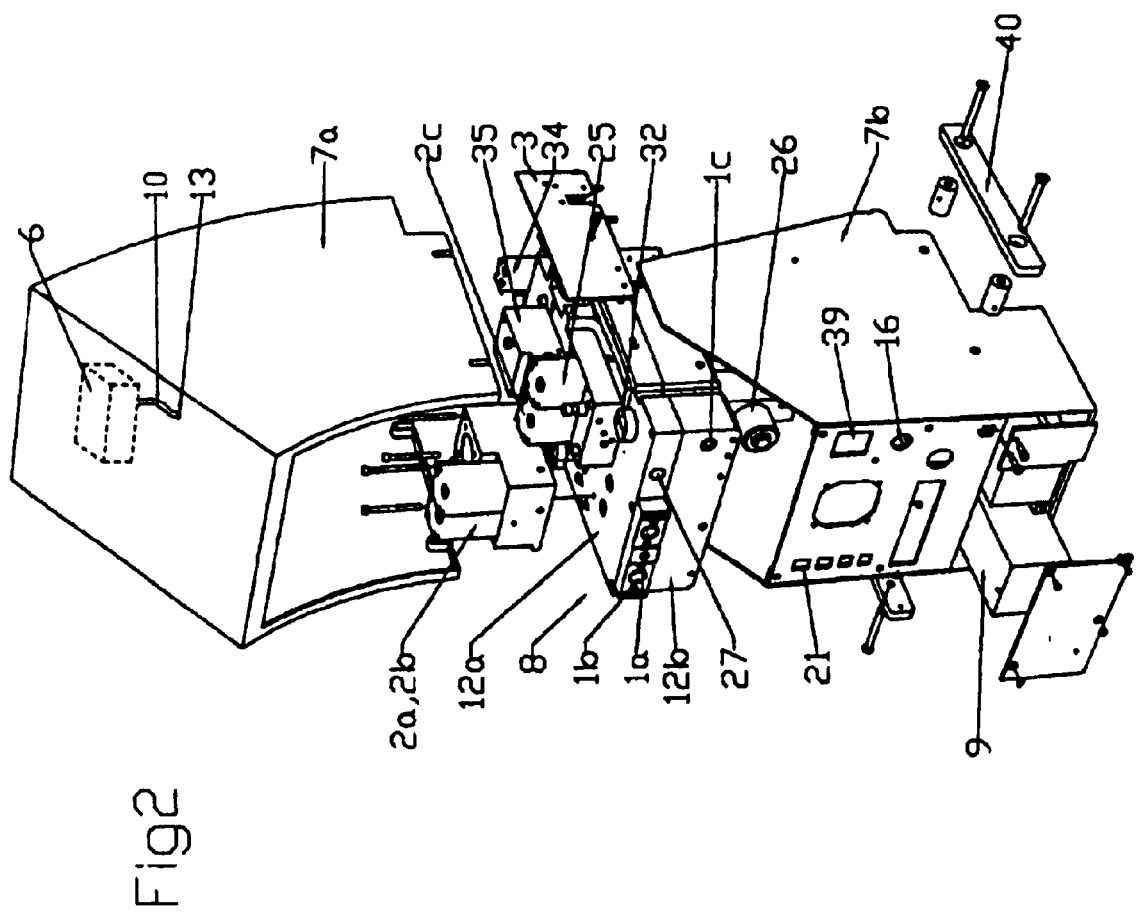
FIG. 2 The same device in FIG. 1, showing the individual components.

FIG. 2 primarily shows the design in FIG. 3 when it is installed in housing 7, which is illustrated in two sections (7a, 7b) in this sample design. The compressor 6 with its flexible pipe 10 is symbolically illustrated. In the lower section of the housing 7b you can see a compartment with integrated battery 9, the electronics 3 and the location of the DC connection 16, an AC connection 39, as well as an interface 21 for a wide variety of connections, such as RS232, nurse call, etc.

Figure 1:
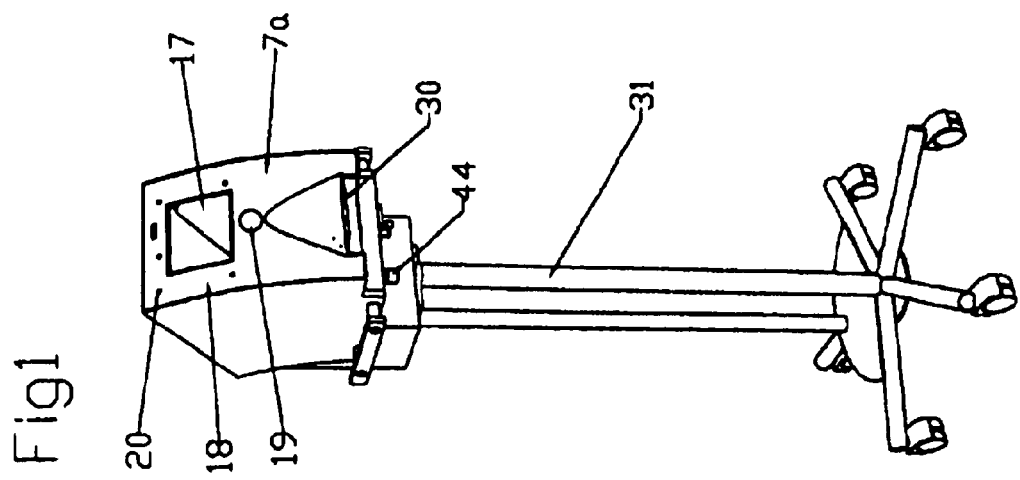
FIG. 1 A new type of ventilator, fully assembled and on a mobile stand.

The grips on the side 40 are used for transportation, as is the stand 31, which is shown in FIG. 1.

In FIG. 1 you can also see a display 17 and a keyboard 18 with push buttons 20 and a preferentially used push-and-turn knob 19. This makes it particularly easy to make the menu-controlled device settings, as mentioned in the introduction to the description.

What is claimed is:

1. A ventilator, excluding anaesthetizing equipment, comprising:
   a closed breathing circuit, comprising:
   a housing with an interior,
   a compact block made of plastic,
   a gas storage integrated in the block,
   at least one ventilator connection,
   at least one compressed air connection,
   at least one valve,
   at least one control system for the at least one valve,
   a ventilating tube,
   at least one connection for the ventilating tube,
   gas pipes in the interior of the housing that connect the gas supply container with the at least one valve and the ventilator gas connection and the ventilator tube connection,
   wherein the majority of the gas pipes are rigid pipes and are integrated in the block together with the gas supply container, and wherein the at least one valve and the at least one connection for the ventilating tube and the ventilator gas connection are integrated in the block.

2. The ventilator according to claim 1, further comprising a compressed gas pipe, and a compressor having an output within the housing, which compressor is connected to the gas storage directly or indirectly via the compressed gas pipe.

3. The ventilator according to claim 2, wherein the compressor is connected to the gas storage by a tube.

4. The ventilator according to claim 2, further comprising at least one heated gas deliverer on the compact block that is heated via compressor waste heat.

5. The ventilator according to claim 4, wherein the gas deliverer comprises at least one of a pipe of at least 100 mm in length within a wall of the gas storage and a tube of at least 100 mm in length that protrudes into the gas storage.

6. The ventilator according to claim 1, further comprising a compressor, wherein the at least one control system comprises a set of electronics that, on an electrical side, permits at least three different modes of operation, either separately or combined.

7. The ventilator according to claim 6, in which the modes of operation comprise at least one of an AC connection to an external power supply, a DC connection to a DC supply or an external battery, and a battery or accumulator connection to an internal battery.

8. The ventilator according to claim 1, wherein on a gas delivery side, the ventilator permits at least three different modes of operation, either separately or combined.

9. The ventilator according to claim 8, wherein the different modes of operation comprise at least one of an external compressed air supply or a compressed air bottle; a compressed air connection via an integrated compressor; a ventilation gas connection to an external ventilation gas supply or to an external ventilation gas bottle; and a therapy gas connection to an external therapy gas bottle.

10. The ventilator according to claim 1, wherein parallel to a ventilation gas or compressed gas deliverer, a therapy gas deliverer is provided via at least one rigid pipe that is separated from other gas deliverers.

11. The ventilator according to claim 10, wherein the therapy gas deliverer is adjustable using the same electronics as the ventilation gas or compressed gas deliverer and the rigid pipe is integrated in the block.

12. The ventilator according to claim 10, wherein the therapy gas deliverer delivers therapy gas and has at least one electronically controlled therapy gas valve via which therapy gas is measured through the ventilating tube proportional to patient gas flow, and wherein the therapy gas is only mixed with the patient gas flow in close proximity to the patient.

13. The ventilator according to claim 1, further comprising, an electrical control system,
wherein an internal power supply is assigned to the electrical control system and the compressor within the housing, and
wherein the input of the power supply is connected to the output of at least one integrated charging equipment that permits input of at least two different types of power feed.

14. The ventilator according to claim 13, wherein the internal power supply comprises an accumulator or a battery.

15. The ventilator according to claim 13, wherein an input of the charging equipment is connected to a manipulation and interrupt-free AC source with a voltage or voltage range of between 80 and 270 volts.

16. The ventilator according to claim 13, wherein an input connection is provided for connection to a DC power supply.

17. The ventilator according to claim 15, wherein an input connection is provided for connection to a DC power supply.

18. The ventilator according to claim 1, wherein the block has least one integrated sensor fox device control.

19. The ventilator according to claim 1, wherein the at least one control system comprises software that is programmed via a control panel and allows setting sigh ventilation for a patient at a selected time interval and a selected sigh volume.

20. The ventilator according to claim 12, wherein the therapy gas uses its own therapy gas output.

21. The ventilator according to claim 20, wherein the sigh ventilation is set for a selected sigh ventilation pressure.

22. The ventilator according to claim 1, further comprising a nebulizer connection or a nebulizer pipe,
wherein the control system comprises software that is programmed via a control panel that, during, operation, controls a nebulization function via the nebulizer pipe and via at least one program-controlled nebulizer valve in such a way that nebulization can be set at certain intervals and a duration can be set during nebulization.

23. The ventilator according to claim 22, wherein nebulization depends upon the patient's inspiratory dynamics.

24. A ventilator comprising:
gas pipes, gas storage, a compressor, electrical or electronic control systems, and
a battery,
all of which are integrated in one block,
wherein the ventilator further comprises emergency backup features that ensure ventilation continues when at least one of an external electrical or pneumatic supply from the compressor fails.

25. A ventilator according to claim 19, wherein parallel to the ventilation gas or compressed gas deliverer, a therapy gas deliverer is provided via at least one rigid pipe that is separated from other gas deliverers.

26. The ventilator according to claim 25, wherein the therapy gas deliverer is adjustable using the same electronics as the ventilation gas or compressed gas deliverer, and
wherein the rigid pipe is integrated in the block.

27. The ventilator according to claim 26, wherein the therapy gas uses its own therapy gas input.

28. The ventilator according to claim 25, wherein the therapy gas delivery has at least one electronically controlled therapy gas valve via which therapy gas is measured through the ventilation tube proportional to patient gas flow, and wherein the therapy gas is only mixed with the patient gas flow in close proximity to the patient.

29. The ventilator according to claim 6, wherein the modes of operation are command free and continuously interchangeable.

30. The ventilator according to claim 8, wherein the modes of operation are command free and continuously interchangeable.

* * * * *

UNITED STATES PATENT AND TRADEMARK OFFICE
CERTIFICATE OF CORRECTION

PATENT NO. : 6,782,888 B1
APPLICATION NO. : 09/958520
DATED : August 31, 2004
INVENTOR(S) : Harri Friberg et al.

It is certified that error appears in the above-identified patent and that said Letters Patent is hereby corrected as shown below:

Please amend claim 1 as follows:

Column 4, Claim 1, Line 55, insert --gas-- after "ventilator"

1 (currently amended). A ventilator, excluding anaesthetizing equipment, comprising:
a closed breathing circuit, comprising:
a housing with an interior,
a compact block made of plastic,
a gas storage integrated in the block,
at least one ventilator gas connection,
at least one compressed air connection,
at least one valve,
at least one control system for the at least one valve,
a ventilating tube,
at least one connection for the ventilating tube,
gas pipes in the interior of the housing that connect the gas supply container with the at least one valve and the ventilator gas connection and the ventilator tube connection, wherein the majority of the gas pipes are rigid pipes and are integrated in the block together with the gas supply container, and
wherein the at least one valve and the at least one connection for the ventilating tube and the ventilator gas connection are integrated in the block.

Signed and Sealed this

Twenty-fifth Day of December, 2007

JON W. DUDAS
*Director of the United States Patent and Trademark Office*